July 8, 1958 A. V. PIKE Plant Pat. 1,727
HYBRID BUDDLEIA PLANT
Filed July 26, 1956
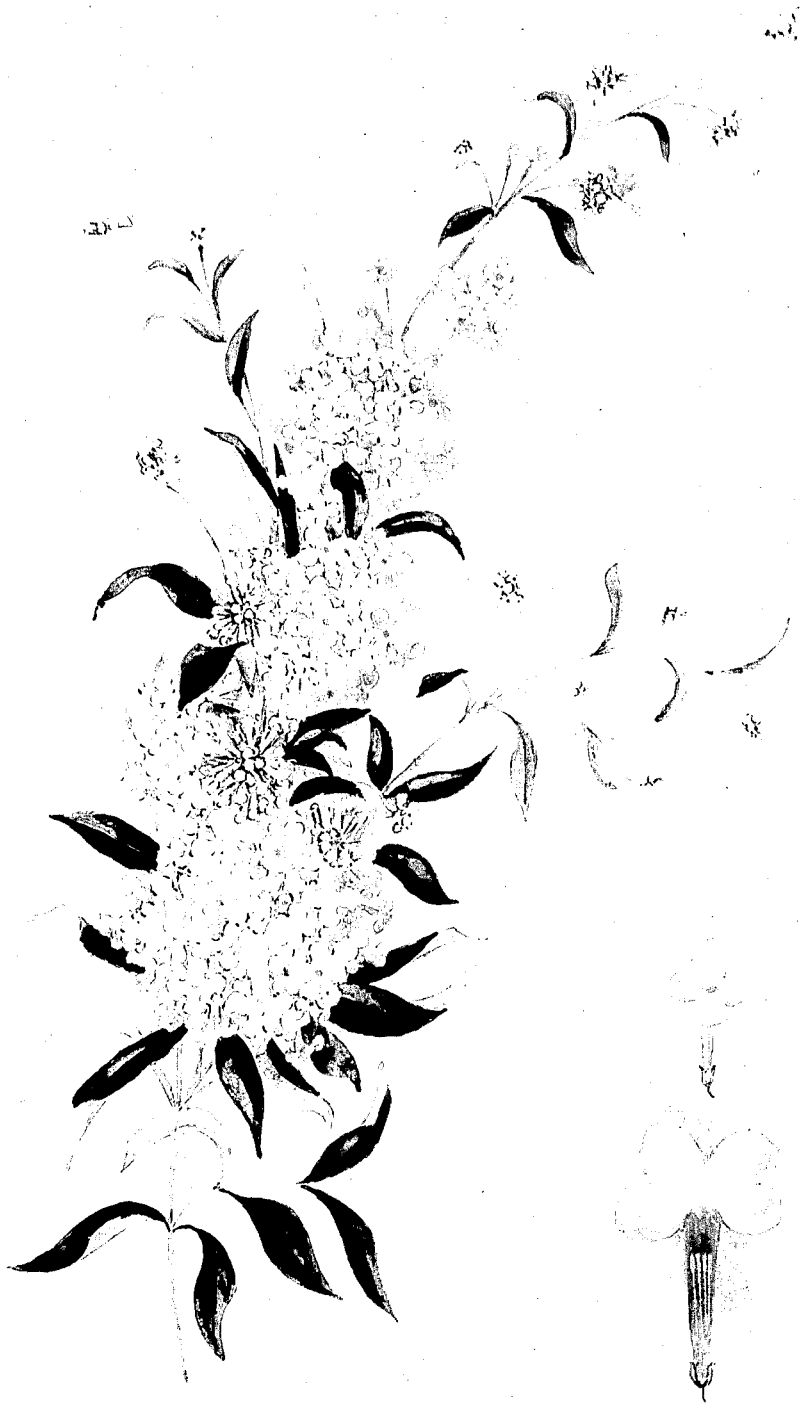

United States Patent Office

Plant Pat. 1,727
Patented July 8, 1958

1,727

HYBRID BUDDLEIA PLANT

Albert Victor Pike, Chiddingstone, England, assignor to John J. Grullemans, Cleveland, Ohio Application July 26, 1956, Serial No. 600,359

1 Claim. (Cl. 47—60)

This invention relates to a new and distinct hybrid species of Buddleia plant.

The present Buddleia plant was developed by the intentional crossing of a *Buddleia caryopteridifolia* plant, as the seed or pistillate parent, with a *Buddleia alternifolia* plant, as the pollen or staminate plant. Neither of the parent varieties is patented. Both parents are true species and natives of China. The present plant is a selected one of the seedlings resulting from the controlled crossing.

The new plant was first asexually reproduced by me at Chiddingstone, Kent, England, from soft wood cuttings which were rooted in the conventional manner.

THE DRAWING

In the drawing, the large central figure is an illustration, on a reduced scale, of a terminal portion of a branch of the plant with some terminal inflorescences in bloom thereon;

The upper one of the two small illustrations is a view of one of the florets of the plant substantially to true scale; and, The larger one of the two small illustrations is an enlarged longitudinal sectional view through one of the florets showing the stamens and the interior of the tube.

THE ROOT OF THE PLANT

The plant has the usual size and spread of Buddleia roots, quite generally comprising a dozen or so main roots with fibrous laterals.

The main roots are of average size for Buddleia plants, the larger roots penetrating more deeply than the fibrous laterals.

The roots have a lateral spread about equal to that of the exposed plant. They are very hardy, having withstood temperatures of 25° below freezing in a cold heavy clay soil which is saturated in winter and desiccated in summer.

THE EXPOSED PLANT STRUCTURE

The plant is a bushy shrub and very hardy. In growth it is partially upright though somewhat spreading, and partially open and loose. The top varies in shape from irregular to rounded or globular.

The plant grows to a height of about five to six feet and to about three to four feet through for three-year old plants, this being quite usual for Buddleias.

The plant is very vigorous in growth.

The plant prefers an open site with average sunshine. The exposure is immaterial. It prefers a deep natural loam which is not too rich and which has normal drainage.

THE PARTS OF THE EXPOSED PLANT

*The main stalks and branches*

The main stalks grow generally upright but slightly arching. They are very much branched and are relatively stiff and tough so that they support the foliage and bloom well. They grow to a length of four feet in a year's growth.

The new growth is a pale greyish green, the old growth being brown, and striated and maculated and somewhat greyish, the smaller terminal portions being comparable in color to Maerz and Paul Plate 10–B–4. The old wood is relatively rough with shaggy bark. The main stalks in groups of three to six rise directly from the ground level.

The branches of the main stalks are generally oppositely arranged with occasional alternate branches. They have a smooth surface texture and are produced abundantly. They are relatively stiff, tough, and flexible, and are adequate to support the bloom and foliage well. Generally they are quite long and straight, but slightly arching at their outer ends.

FOLIAGE

The foliage is generally dense and abundant. The leaf arrangement is mostly opposite, though occasionally alternate and even whorled, apparently due to the fact that one of the parents has opposite leaves and the other alternate leaves.

The new leaves, on their upper faces are fern green comparable to Maerz and Paul Plate 21–I–7. They are less greyish on the bottom.

The old leaves, on top, are green comparable to Maerz and Paul Plate 23–L–7 and, on the bottom, a more verdant green comparable to Maerz and Paul Plate 27–A–3. The color of both the old and new leaves is generally uniform.

The leaves are mostly of average size, some being large and ranging from about four to eight inches in length and some being shorter, and ranging from one-half inch to two and one-half inches in width. The minimum length is about one and one-half inches.

They are generally oblong lanceolate with dentate margins at the base merging into even serrated margins toward the apex. The apex generally is acute. The leaves are of average thickness with glabrous upper faces and smooth, downy lower faces. Occasionally the leaves take after the male parent in which case they are entire and linear-oblong.

The peticels are pale green and concave, averaging about ¼″ in length. They have a smooth surface texture and are quite strong. There appears to be generally an embryo shoot in each leaf axil.

THE BLOOM

The plant, in the central north temperate zone, blooms continuously for about two months, beginning in early August, and then intermittently for a total blooming period of about three and one-half months thereafter.

The spikes of the blooms last about two and one-half weeks as cut flowers. Only a small percentage of seeds are set so that cutting does not alter the amount of blooms produced.

The buds are small and globular with a pubescent aspect. They are a lilac purple when the petals begin to unfurl changing to a lilac pink when half blown. Before opening they are of a green, comparable to Maerz and Paul Plate 18–D–4.

The calyxes or bud coverings are four cleft at the apex and of the usual size and type, being about ⅛″ long and having a pubescent surface.

The peduncles of the flower average from six to eighteen inches in length and are minutely hirsute or wooly because of fine greyish-white tomentum. They are light brown masked by greyish white tomentum. They are very strong.

The individual florets do not have any pedicels but are sessile on the terminal and auxiliary subpeduncles.

The higher the temperature the more rapidly the florets open. The individual florets average about two-fifths of an inch in diameter. They are borne in tens of thousands on each plant.

The inflorescences as a whole are borne in thryse-like spikes. The individual inflorescences of the plant last from three to four weeks when uncut and from two to two and one-half weeks when cut.

The florets have the usual four petals or limbs and are of cruciform shape. In color, the florets are what may be termed a lilac pink, the petals ranging on the upper surface from a light shade, comparable to Maerz and Paul Plate 41–B–3 through Plate 41–D–4, through Plate 41–E–5. They have orange centers comparable to Maerz and Paul Plate 3–I–11.

The reverse of the petals is a mauve.

The general tonality from a distance is a kind of mauve blue.

There is little change in color during the blooming season. When changes do occur, they run successively from a lilac mauve through a light purple to a light pink and then fade to a mauve.

The petals are of smooth texture, being more intense in color inside than outside. They have the usual form, being nearly flat and partially convoluted. The four limbs or petals of each floret extend into a cylindrical corolla about one-third of an inch long which is substended by the four cleft calyx. The florets are very similar to those of both parents. The outside of the tube is Formosa, comparable to Maerz and Paul Plate 12–A–8. The inside of the tube is an orange comparable to Maerz and Paul Plate 3–I–11.

The flower has a medium fragrance of first class quality which is very lasting on the cut flowers as well as on the growing flowers.

The stamens are simple and unbranched and generally straw colored. Usually there are three or four bivalved stamens which are adnate to the inside of corolla. The pollen is an ivory, comparable to Maerz and Paul Plate 10–B–2. The styles are white flushed with purple and are about one-sixteenth of an inch long. The stigmas are about one-sixteenth of an inch long and are deep green and viscid. Ovaries are very sparse, there usually being only one which is nearly globular and which is green and glabrous. However, this particular hybrid is fertile and carries viable seeds.

The asexual reproduction hereinbefore referred to was by means of cuttings of half-ripened wood in accordance with the following procedure: Cuttings of half-ripened lateral shoots, which are side growths of young wood which are just beginning to become firm at the base, were taken off the parent with a heel of the older wood and then inserted into sandy compost in a propagating case. These cuttings were kept in a moist, confined atmosphere until rooting took place. They were also shaded from intense sunlight. After the rooting took place, ventilation was admitted to the case and the rooted plants subsequently were potted off singly to form separate individuals.

The present variety of Buddleia plant is characterized particularly in that it is one of the latest flowering of all known Buddleia species or hybrids. It embodies the best attributes of both parents and in fact excels both as to aroma, vigorousness, and large size of flower trusses. It is a good grower with no propensity to suddenly die out. The aroma is believed to be the best of all Buddlerias except the very tender Indian species known as Buddleia asiatica which latter cannot be grown out of doors. The plant accommodates itself well to varying conditions and flowers just as profusely when grown as a standard or unpruned bush as when pruned for later flowering. It can be propagated readily from cuttings of soft half-ripened wood and also cuttings from ripe wood, though this cannot be done with the parents.

I claim:

The new distinct hybrid species of Buddleia plant as herein described and illustrated.

No references cited